(12) United States Patent
Saito et al.

(10) Patent No.: US 6,258,128 B1
(45) Date of Patent: Jul. 10, 2001

(54) ARTIFICIAL LEG HAVING BEARING WITH STOPPER

(75) Inventors: Makoto Saito; Syuji Hagihara; Hiroki Nakayama, all of Kobe (JP)

(73) Assignee: Kabushiki Kaisha Kobe Seiko Sho, Kobe (JP)

( * ) Notice: Subject to any disclaimer, the term of this patent is extended or adjusted under 35 U.S.C. 154(b) by 529 days.

(21) Appl. No.: 08/574,544

(22) Filed: Dec. 19, 1995

(30) Foreign Application Priority Data

Dec. 27, 1994 (JP) .................................................. 6-324651
Jun. 30, 1995 (JP) .................................................. 7-165705

(51) Int. Cl.[7] ...................................................... A61F 2/64
(52) U.S. Cl. .............................................................. 623/39
(58) Field of Search ................................ 623/43–46, 36, 623/37, 39–42, 38, 33, 34; 602/26, 16

(56) References Cited

U.S. PATENT DOCUMENTS

| 278,566 | * | 5/1883 | Lewis ................................ 623/46 X |
| 792,711 | * | 6/1905 | Koeber ................................... 623/45 |
| 2,452,459 | * | 10/1948 | Hanger, III . |
| 2,542,567 | * | 2/1951 | Peters . |
| 2,551,537 | * | 5/1951 | Havens . |
| 2,568,053 | * | 9/1951 | Catranis . |
| 2,698,947 | * | 1/1955 | Dumelin ............................... 623/44 |
| 3,673,613 | * | 7/1972 | Asbelle et al. . |
| 4,549,318 | | 10/1985 | Takahama . |
| 4,802,467 | * | 2/1989 | Pansiera ............................ 623/39 X |
| 5,326,353 | * | 7/1994 | Franklin . |

FOREIGN PATENT DOCUMENTS

| 178421 | * | 5/1954 | (AU) . |
| 1143966 | * | 2/1963 | (DE) ..................................... 623/39 |
| 723494 | * | 4/1932 | (FR) ..................................... 623/39 |
| 490121 | * | 8/1955 | (IT) ..................................... 623/39 |

OTHER PUBLICATIONS

Nadar; M. (editor): Otto–Bock–Prothesen–Kompendium: Prothesen fur die untere Extremitat. Technical publishing house Schiele & Schon GmbH, 1987, pp. 37–45.*

* cited by examiner

Primary Examiner—David H. Willse
(74) Attorney, Agent, or Firm—Oblon, Spivak, McClelland, Maier & Neustadt, P.C.

(57) ABSTRACT

An artificial leg capable of functioning as an "intelligent artificial leg" is and having a knee joint bearing member and stopper to which only a small moment is applied on the lower leg frame when the leg is standing or the knee is bent, and the lower leg frame has a uniform thickness and is lightweight yet with no loss of strength, and further the protuberances of the inner and outer circumferential surfaces of the the lower leg frame are small and, the empty space within the the lower leg frame has been widened.

A rotating stopper 5 for standing, a rotating stopper 6 for bending the knee and a knee joint bearing member 4 are formed integrally within the the artificial leg and a knee joint bearing member 4 is embedded within said lower leg frame 1.

7 Claims, 13 Drawing Sheets

ARTIFICIAL LEG HAVING BEARING WITH STOPPER

BACKGROUND OF THE INVENTION

1. Field of the Invention

This invention relates to an artificial leg for assisting thigh amputees to walk, and relates in particular to an original structure for a knee joint bearing to connect the thigh and lower leg of the artificial leg.

2. Description of the Related Art

The artificial leg is an artificial limb for assisting amputees to walk, who have lost their natural leg from the thigh on downwards. In recent times, in attempts to restore to the amputee the same walking ability of physically able person, so called "intelligent artificial legs" have been proposed, housing drive mechanisms to move the lower leg in an action linked with the walking action of the thigh.

In order to provide the user of the artificial leg with as comfortable a feeling as possible, efforts were made to obtain an artificial leg with a weight equal to or within the weight of a human leg, however the intelligent leg, and in particular the mechanism housed in the lower leg portion for driving the said lower leg portion, have special characteristics which limit the extent to which the weight can be reduced, therefore making a light weight frame for the lower leg (hereafter simply referred to as the lower leg frame) necessary instead.

Therefore in the conventional art, the lower leg frame used metal materials such as aluminum alloys because of advantages such as ease of machining and high strength for achieving a lower leg frame in an artificial leg which could support the weight of the user. However, these metallic materials had the drawback of increased weight so that as one countermeasure, frames made of fiberglass providing comparatively good strength and comparatively good rigidity were commercially marketed in Europe and America.

The living habits of the user impart a large effect on the structure of the lower leg frame made of fiberglass. Design standards for strength in the artificial leg use ISO standards which in particular require as a safety margin, sufficient strength to withstand four times the weight of the user while standing. This means an exceedingly high moment acts on the knee joint bearing of the frame. However these ISO standards are based on the living habits in Europe and America where the leg is mainly used for standing and sitting in chairs, so that the main force on the lower leg frame is an axial compressive force on the lower leg frame while standing, and the moment on the knee joint bearing.

In contrast, in addition to the above, daily living in Japan, call for sitting on bent knees ("seiza") as a common part of everyday life. Therefore during this "seiza" posture (hereafter referred to as "bent knees or kneeling") an exceedingly large moment is applied in the reverse direction when standing, acting on the knee joint and the periphery of the knee joint of the lower frame. Therefore artificial leg design must also reflect the need, for handling a large moment on the knee joint bearing of the frame when the knee is bent.

Figure 9:
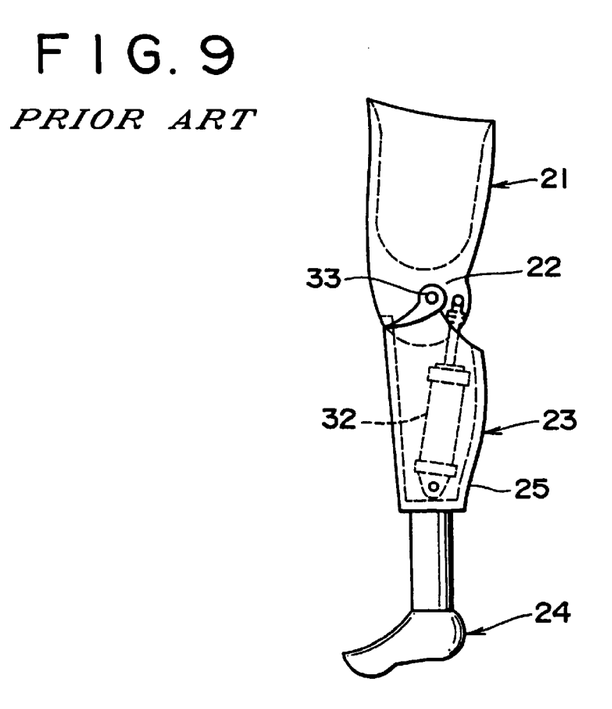
FIG. 9 is one example of an artificial leg of the conventional art.

More specifically, as shown in FIG. 9, this kind of artificial leg comprises a socket 21, a lower leg 23 and a foot 24. The inside of lower leg frame 25 of the lower leg 23 houses a cylinder 32 for driving the artificial leg itself, an energy source (not shown) for driving the said cylinder 32, and drive mechanisms such as valves and control equipment. The socket 21, and lower leg 23 along with a knee joint member 22 equivalent to the human knee joint, are connected for free rotating movement.

Figure 10A:
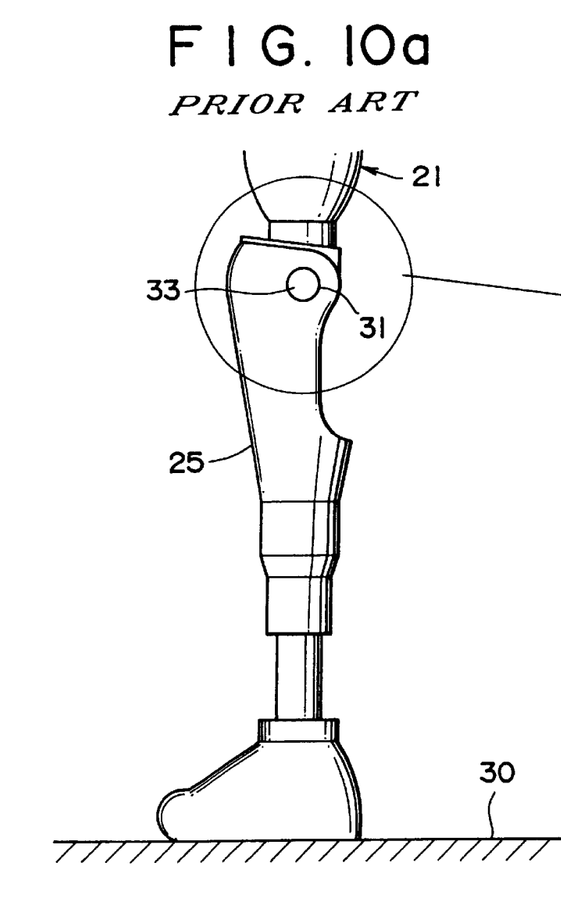
Figure 10B:
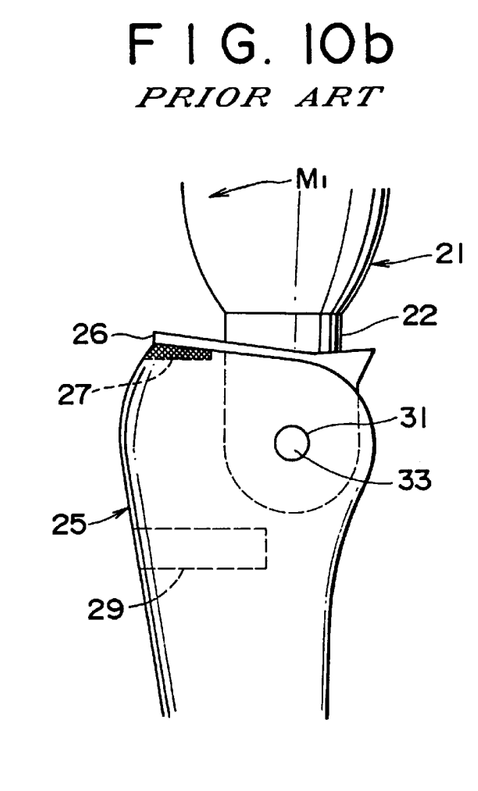
Figure 11A:
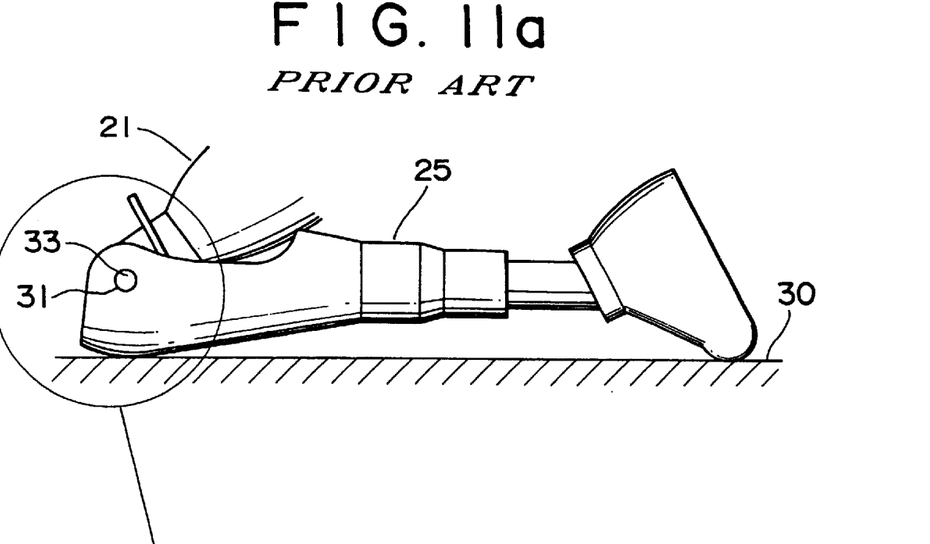
Figure 11B:
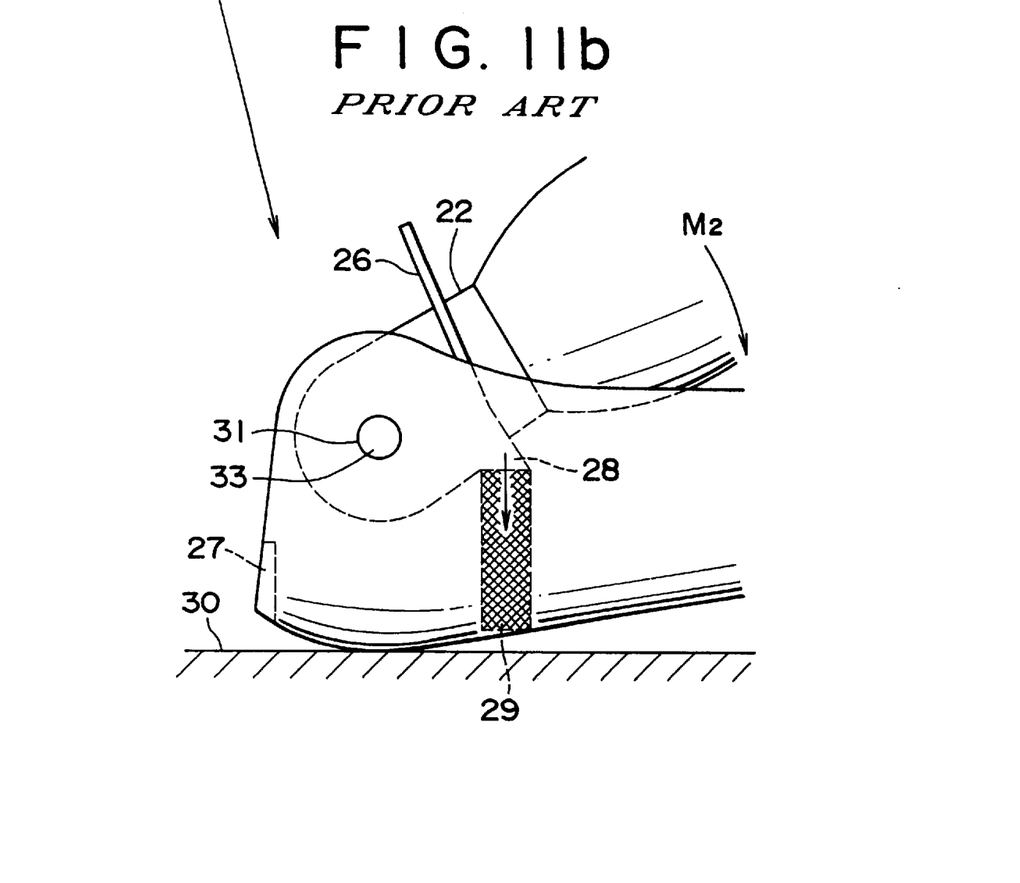

As shown in further detail in FIGS. 10 and 11, a stopper 26 for protrusion into knee joint member 22 during standing, is provided at the upper end of the lower leg frame 25 to contact a stopper 27 on the fixed side, further, a stopper 28 for protrusion into knee joint member 22 during bending, is provided at the inner wall of the lower leg frame 25 to contact a stopper 29 on the fixed side, and said stopper 29 is secured with respect to the lower leg frame 25 by means of a tightening means of machine screw and bolts (not shown) etc.

In current intelligent artificial legs, as shown in FIGS. 10(a) and 10(b), during standing of the knee joint member 22, the stopper 26 makes contact with the stopper 27 on the fixed side in the lower leg frame 25, the rotation to the front side of the socket 21 is stopped, and the standing position is maintained. When at this time, a compressive force is applied axially based on the weight of the user to the lower leg frame 25, an additional force in terms of a rotating moment M1 shown by the arrow M1 in the Figure, is applied to the vicinity of the knee joint bearing 31 of lower frame leg 25, using the fixed side stopper 27 as a support point. On the other hand, in the bent knee position in FIGS. 11(a) and 11(b), the stopper 28 makes contact with the fixed side stopper 29 installed in the lower leg frame 25, the excess rotation of the socket 21 to the floor 30 is stopped and a kneeling posture is maintained. However the load at this time on the lower leg frame 25 based on the weight of the user is applied only as rotating moment M2 along an axis 33 with the fixed side stopper 29 as a support point, and as a result, a colossal rotating moment M2 due to the weight of the user is applied in the vicinity of the knee joint bearing 31. In addition, when the artificial leg is standing, a lateral moment is applied in the vicinity of the knee joint bearing 31, in addition to the above mentioned rotating moment M1.

As can be clearly understood from FIGS. 10(a), 10(b) and FIGS. 11(a), 11(b), the rotating moment on the lower leg frame 25 acts in completely opposite directions according to the posture of the user and an exceedingly large stress is generated in the lower leg frame 25 in the vicinity of the knee joint bearing 31. Therefore the need to provide adequate strength in terms of thicker plate to support the axis 33 of said lower leg frame 25 proves unavoidable thus hindering attempts to make the lower leg frame 25 light weight.

As previously explained, the said rotating moment and the lateral moment make it necessary to support the lower leg frame of the artificial leg. However since an exceedingly large stress is generated in the support section, the thickness generally has to be altered according to the stress acting on the frame shape. When molding fiberglass parts where the thickness varies in different sections, the molding efficiency is poor because of the difficulty in obtaining a uniform injection of fiberglass. In particular, when forming protrusions and angular sections to adequately strengthen the crucial knee joint, in many cases the fiberglass does not sufficiently fill into the corners of a particular section and the part has inadequate strength to withstand the application of a high stress force. These protrusions in the inner and outer circumferential surface of the lower frame are not desirable because of bad effects on the outer appearance and since this is an artificial leg, a rather wide internal space is needed to house the drive mechanism inside the lower leg frame in order to operate the lower leg.

SUMMARY OF THE INVENTION

In view of the need to resolve the foregoing problems, it is an object of this invention to provide an intelligent artificial leg which; disperses the moment applied in the vicinity of the knee joint bearing of the lower leg frame occurring from a compressive load caused by the weight of the user applied during standing or bending and, reduces the moment applied to points within the surface area of the lower leg frame and, achieves an overall uniform thickness without reducing the strength of the lower leg frame to make a lighter weight possible and, further reduces protrusions on the inner and outer circumference of the frame and provides a widened space inside the frame.

Another object of the invention is to provide artificial leg mounted consisting of a socket which holds a thigh section and a lower leg frame having a foot fastened at the bottom, mutually connected for freely rotating axial movement in which; a knee joint member is integrally formed with a stopper to regulate rotation of the socket during standing and bending of the knee, and besides said stopper being imbedded in the lower leg frame to protrude out from the side wall of the lower leg frame, an engaging stopper is provided to engage with said stopper in the rotating section of the socket mutually connected for freely rotating axial movement in the lower leg frame.

Yet another object of the invention is an artificial leg in which a knee joint bearing member is formed of polygonal shapes such as that of a triangle, rectangle, hexagon or octagon, and each corner of the knee joint bearing member is formed in an arc.

A still further object of the invention is an artificial leg in which, a knee joint bearing member is formed in eccentric shapes of an oval, ellipse, or egg.

An additional object of the invention is an artificial leg in which, the knee joint bearing member is made to incline 45 to 75 degrees forward and downwards relative to the perpendicular axis of the lower leg frame, and said knee joint bearing member is embedded in the lower leg frame.

A yet additional object of the invention is an artificial leg in which, a flange is provided, and a knee joint bearing member 0.6 to 1.0 mm thicker than the lower leg frame is cooled and embedded in the lower leg frame.

The stopper for standing and the stopper for kneeling are integrated into the knee joint bearing member, and a compressive force applied axially based on the weight of the user by means of the knee joint bearing member embedded in the lower leg frame, and a rotating moment applied to the lower leg frame in a direction completely opposite the stance of the user are dispersed in the lower leg frame.

Restated, the compressive force acting on the lower frame and the rotating moment are supported by a wide contact surface at the knee joint bearing member, and the load from the compressive force added axially to the lower leg frame and rotating moment are dispersed and reduced at individual points over the surface area.

The weight of the user must be considered when selecting the shape of the knee joint bearing member. Triangular, rectangular and other various eccentric polygonal, gourd, oval, elliptical or egg shapes can be employed but forming of eccentric shapes is particularly desirable for the knee joint bearing member. Reasons for the eccentric shape being the need for receiving and halting the rotating moment, avoiding a concentration of stress in the lower leg frame and effectively dispersing the rotating moment and the compressive force along the axis.

The inventors evaluated the concept of embedding the knee joint bearing member in the lower leg frame in order to reduce as much as possible the application of rotating moment during standing and kneeling of the artificial leg when an eccentric contour was used in the knee joint bearing member.

Figure 12A:
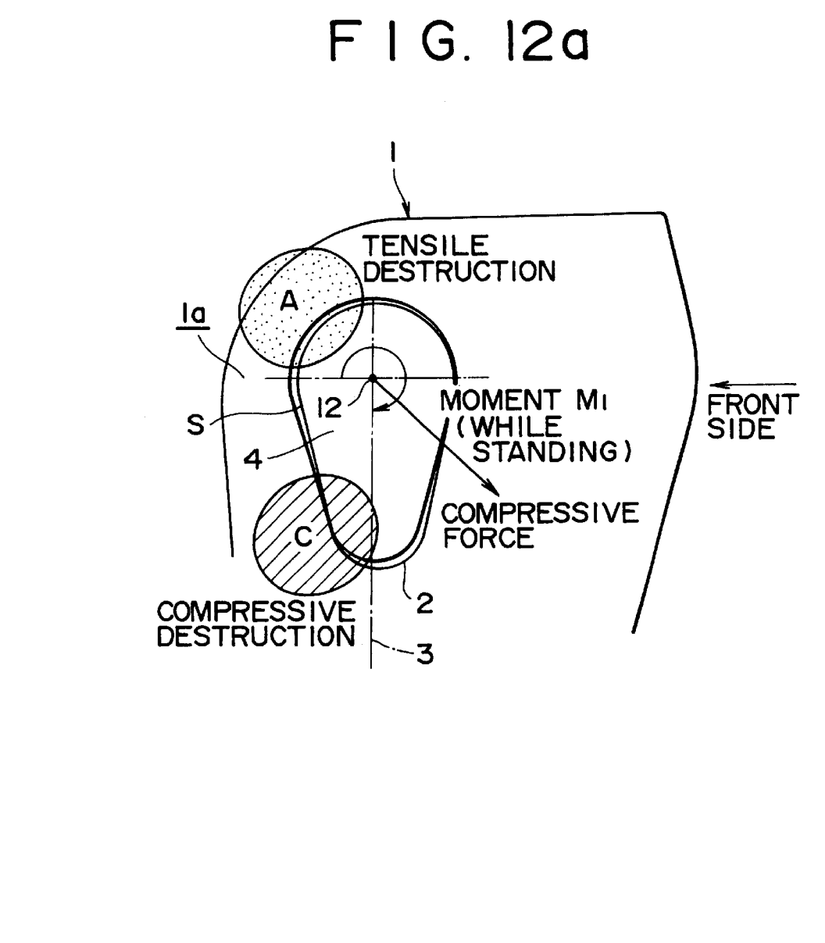
Figure 12B:
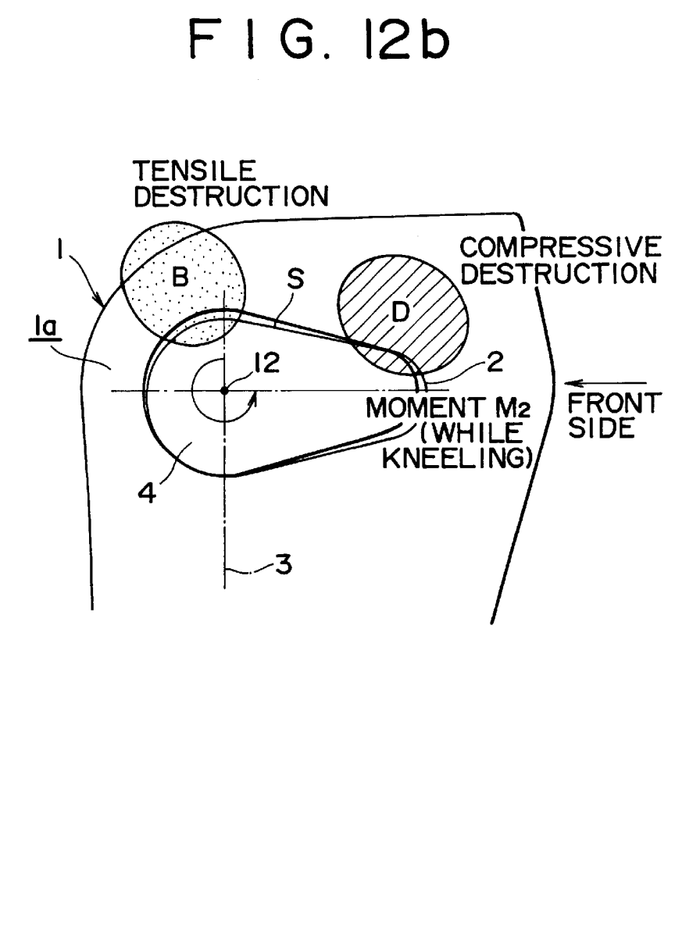

FIGS. 12(a) and 12(b) show a knee joint bearing member 4 made in an eccentric egg shape bound by a common contact line joining two circles with displaced centers. The figures show the action of knee joint bearing member 4 while embedded in lower leg frame 1 in typical positions in which a load is applied to the lower leg frame 1 as for instance in FIG. 12(a) where the knee joint is embedded parallel (0°) to the perpendicular line 3, and FIG. 12(b) where the knee joint is embedded at a right angle (90°) to the perpendicular line 3. In FIG. 12(a) a deformation occurs in lower leg frame 1 due to the rotating moment M1 when standing, a gap S is gradually formed between it and the knee joint bearing member 4 conveying the rotating moment M1 to the upper part of lower leg frame 1, a tensile force occurs at the large circle (A) side of a fringe 1a and a compressive force occurs at the small circle (C). The same tensile force and compressive forces simultaneously occur at positions corresponding to the central axis of knee joint bearing member 4.

Further, a compressive force due to weight of the user acts downwards and forwards from the knee joint axis 12. In this same way in FIG. 12(b), due to the rotating moment when kneeling; a tensile force acts on the upper part of lower leg frame 1 and large circle (B) and a compressive force acts on small circle (D).

As clearly shown by the above, there are two type of destructive force; tensile destruction and compressive destruction acting on the opening 2 of lower leg frame 1 embedding knee joint bearing member 4. Here what should be considered is the maximum load imposed by the tensile force and compressive force caused by the rotating moment acting on the narrow portion in the vicinity of the upper part of lower leg frame 1, in other words the fringe 1a. The directions in which the rotating moment M1 and M2 are applied are different during standing and kneeling but the sum total of tensile forces and sum total of compressive force acting on the said section are equivalent. At any rate it is extremely important that concentration of the load at a localized point be avoided. To prevent destruction of the lower leg frame 1, an important precondition to averting a concentration of colossal stress is the embedding of the knee joint bearing member 4.

Figure 13:
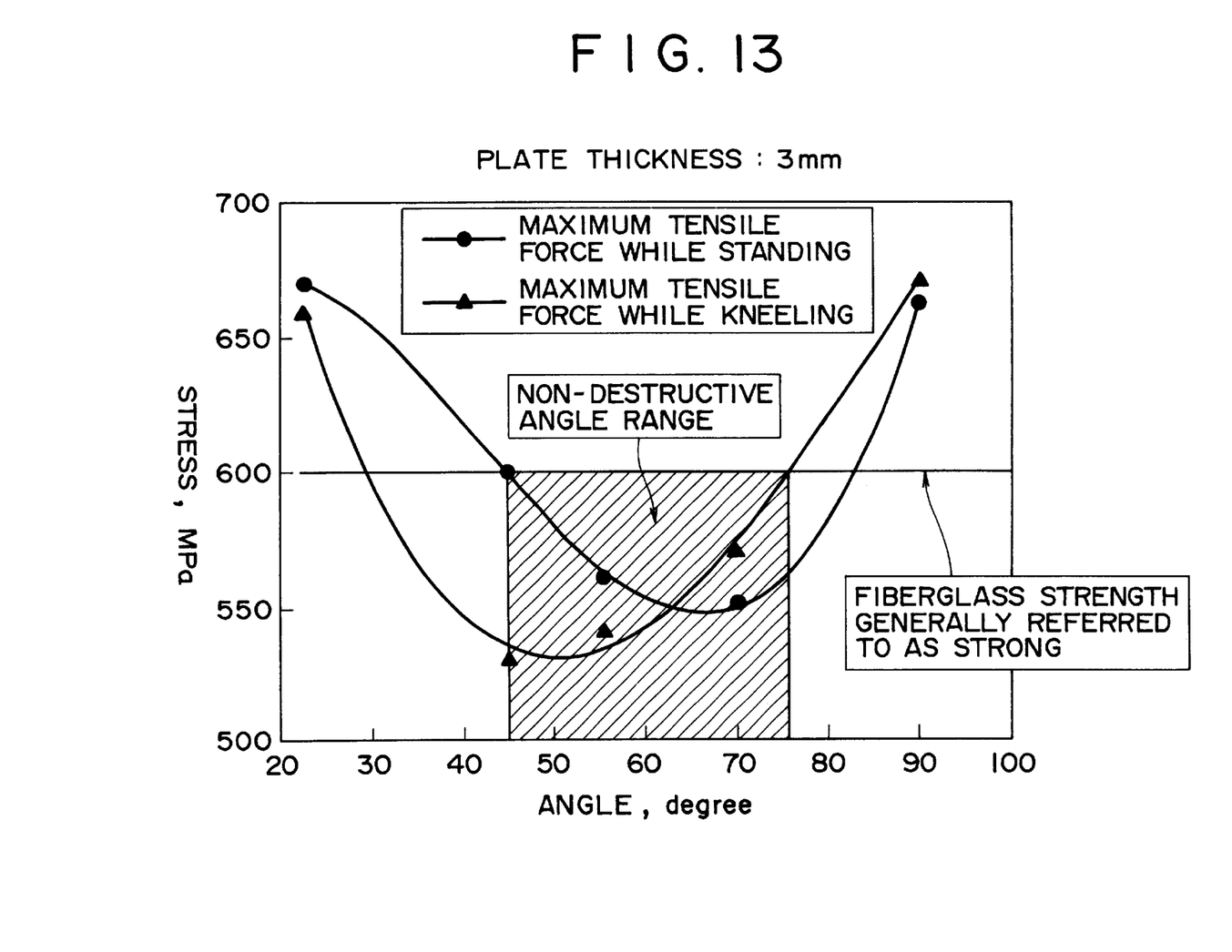
FIG. 13 is a view showing data obtained from finite element analysis of the embedded status of the knee joint bearing member and the tensile force on the lower leg frame.

In consideration of the above FIG. 13 shows data from analysis of maximum stress and embedded position of the knee joint bearing member 4, obtained by finite element analysis based on ISO standards. The object of the stress evaluation was limited to the vicinity of the frame opening and since evaluation of either tensile strain or compressive strain would be sufficient for the strain evaluation, tensile strain was used for the analysis.

A user weight of 100 kg was assumed and a lower leg was formed using 3 mm thick fiberglass the egg-shaped knee joint bearing member 4 having a 7 mm circle with center distance of 24 mm and radius of 12 mm in a common contact line was placed at the rotation center of the artificial leg on the perpendicular line of the lower leg frame 3, a width of 12 mm was maintained for the fringe 1a, and results were obtained by finite element analysis of the maximum stress occurring in the lower leg frame 1 during kneeling and standing by successively changing the installation angle forward (meaning forward of the artificial leg) relative to the perpendicular line of lower leg frame 1.

As analysis results clearly show, as the embedding angle for knee joint bearing member 4 increases, the maximum tensile force during standing and kneeling tends to decline. During standing, a minimum value was shown in the 65° to 75° range, and during kneeling a minimum value was shown in the 45° to 55° range.

On the other hand to order to attain a maximum strength (600 MPa) offered by current fiberglass for the knee joint bearing member 4 installation, if installed in a forward direction of 45° to 75° relative to the perpendicular line 3 of lower leg frame 1, the fiberglass proved sufficiently strong but when allowing for a maximum tensile strain occurring during standing and kneeling, the most effective range for the knee joint bearing member 4 installation relative to the perpendicular line 3 of lower leg frame 1 is preferably 60° to 70°.

The inventors performed finite element analysis of the said knee joint bearing member 4 under a variety of conditions but putting aside consideration of absolute values for maximum tensile stress, the above range of angles proves effective and the installation conditions have been verified as largely applicable to knee joint bearing members of eccentric shape.

However when installing the machine-finished eccentric knee joint bearing member 4 into the opening 2 of machine-finished lower leg frame 1, it is necessary to provide somewhat of a gap. This gap as shown in FIGS. 12(a) and 12(b) must allow for the above installation conditions. When rotating moment M1 and M2 are applied during standing and kneeling, a gap occurs between the opening 2 and the knee joint bearing member 4, this causes a certain amount of "play" to occur. The user may therefore feel the leg is not a good fit.

On the other hand, when this gap S occurs, the knee joint bearing member 4 makes contact with the lower leg frame 1 at two points when rotating moment M1 and M2 are applied. A high contact strain is thus generated on the lower leg frame 1 as above. By eliminating this gap, destruction of the lower leg frame 1 can be avoided. In order to therefore eliminate the gap S, the eccentric knee joint bearing member 4 is installed by being cooled and then fit into the opening 2 of the lower leg frame 1.

A knee joint bearing member 4 made of aluminum is preferable when making a cooling and fitting type installation. Since the aluminum has an expansion rate of 23.7× 10-6/C.°, an aluminum type knee joint bearing member 4 can be cooled and fit into place. Liquid nitrogen is used to cool the knee joint bearing member 4 and contract it, to allow fitting into the opening 2 of the lower leg frame 1. Once the temperature returns to normal, the knee joint bearing member 4 expands and widens with the opening 2, allowing knee joint bearing member 4 to contact the lower leg frame 1 with no gap.

Figure 14:
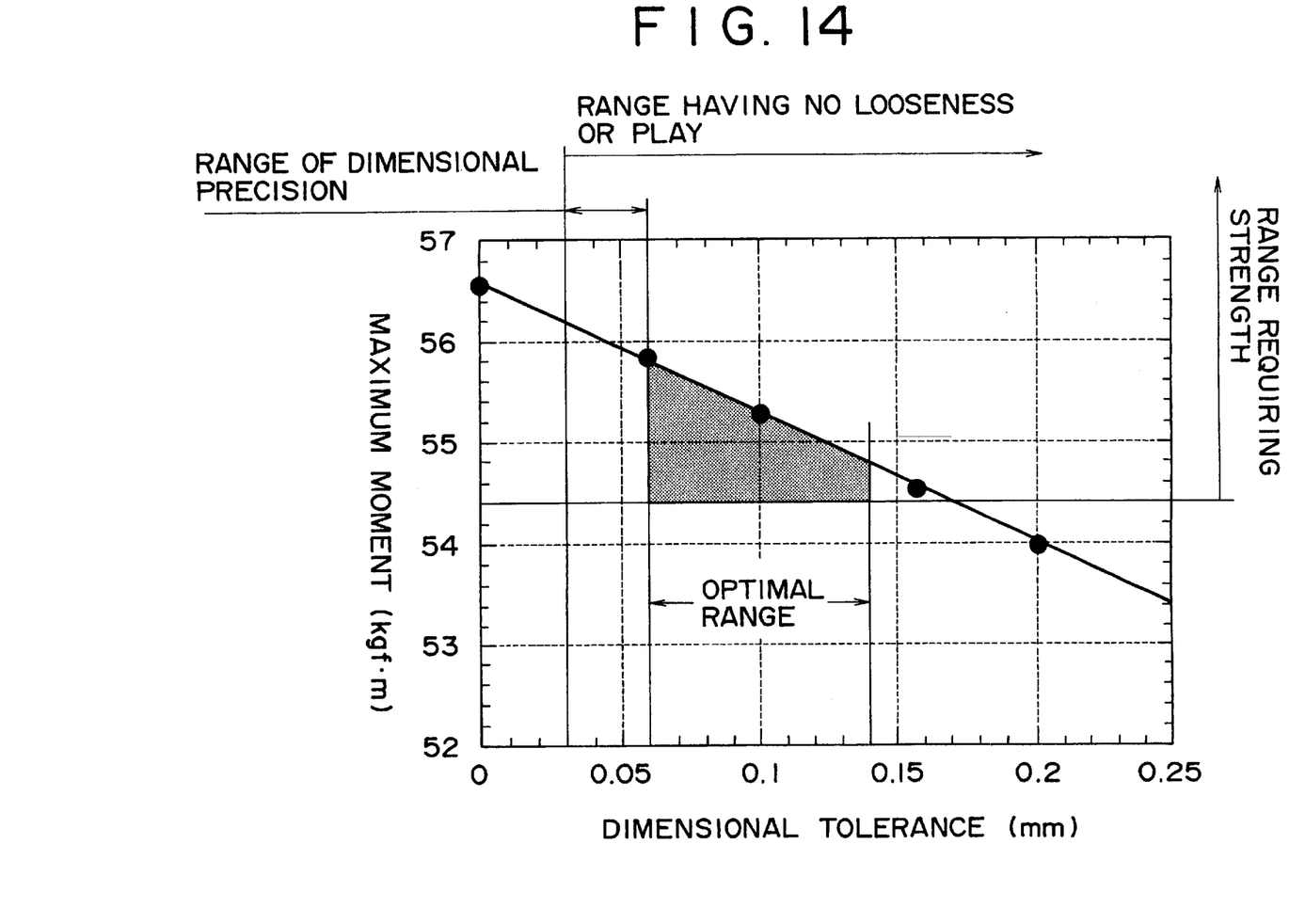
FIG. 14 is a graph showing the relation of the dimensional tolerance between the knee joint bearing member and the opening, and the maximum moment for destruction of the lower leg frame by means of rotation of the knee joint bearing member.

As described above, the cooling and fitting installation applies an expansion force to the opening 2 of lower leg frame 1. When this expansion force is too great the lower leg frame 1 may be prone to damage so that it is essential to control the dimensions of both parts within a fixed range. FIG. 14 shows the relative dimensions of the knee joint bearing member 4 and the opening 2 in relation to the destructive moment on the lower leg frame 1 due to the rotation of the knee joint bearing member 4. With a dimensional precision of ±0.015 during machining, a dimensional tolerance of 0.06 or greater will prove sufficient to maintain a target value for fixed expansion even with minimal dimensional tolerances between the knee joint bearing member 4 and the opening 2. On the other hand when the dimensional tolerance between both parts is greater than 0.17 mm damage to the lower leg frame 1 will occur from the expansion force.

Thus it can be seen that after considering in the machining tolerance, a target value dimensional tolerance of less than 0.14 mm is preferable for both parts. Machining both parts within a dimensional tolerance range of 0.06 mm to 0.14 mm is feasible.

Besides the said rotating moment M1 acting on the eccentric knee joint bearing member 4 during standing, a lateral moment occurs that rotates the knee joint bearing member 4 sideways. As a result, the contact surface area between the lower leg frame 1 and the knee joint bearing member 4 decreases, so that the contact strain in turn increases, making the lower leg frame 1 prone to damage. To prevent this phenomenon, providing a flange on the eccentric knee joint bearing member 4 will prevent rotation of the knee joint bearing member 4 caused by the lateral moment. Further, by decreasing the thickness of the knee joint bearing member 4 to 0.6 to 1.0 mm less than the lower leg frame 1, the contact surface will not decrease even if some rotation of knee joint bearing member 4 occurs, and there will be no increase in the contact strain.

Figure 15:
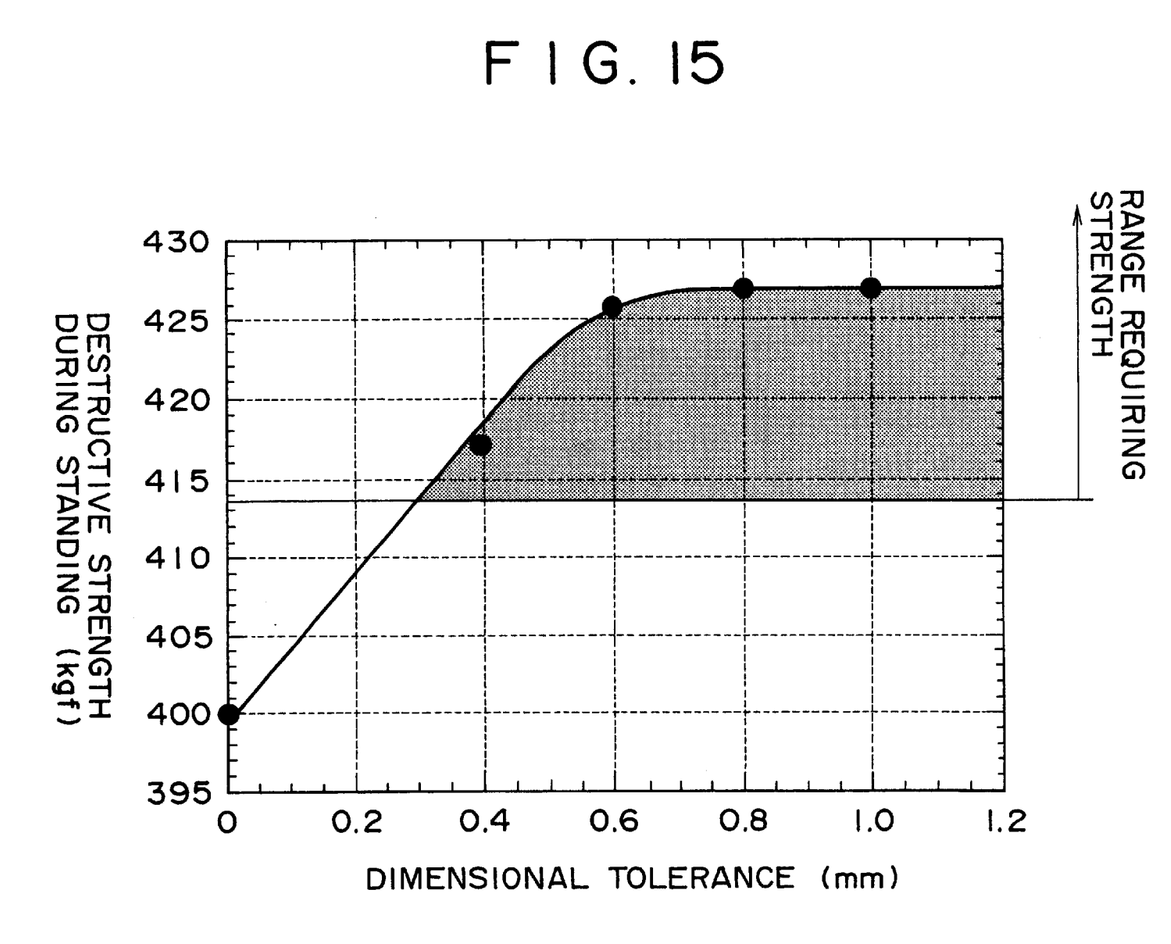
FIG. 15 is a graph showing the relation of the dimensional tolerance between the knee joint bearing member and the lower leg frame thickness, and the destructive load on the lower leg frame occurring from the the rotating moment radially along the axis.

FIG. 15 shows the relation of the dimensional tolerances in thickness of the knee joint bearing member 4 and the lower leg frame 1, and the destructive load on lower leg frame 1 due to the lateral moment applied on the knee joint bearing member 4. When considering the dimensional precision for thickness of the knee joint bearing member 4, the strength provided by a thickness of 0.6 mm or more will prove sufficient without reducing the surface contact area even if some rotation does occur in the knee joint bearing member 4, and the contact strain will not increase. Keeping this thickness within 1.0 mm is also preferable to ensure the object of the invention which is the provision of an intelligent artificial leg.

As the above clearly shows, in the artificial leg of this invention, by providing rotating stoppers in the knee joint bearing member for both standing and kneeling, and employing an embedded structure for the knee joint bearing member in the lower leg frame, the structure of the rotating portion of the artificial leg can be simplified. Further, by eliminating compressive forces from the weight of the user on the lower leg frame and/or rotating and lateral moment by dispersion in the knee joint bearing member without transmission of such forces, a lower leg frame of uniform thickness can be achieved that is light weight yet has no loss of strength. This lower leg frame further has few protrusions on the inner and outer circumferential surfaces allowing a wider internal space to be designed within the lower leg frame providing an artificial leg suitable for use as an intelligent artificial leg.

BRIEF DESCRIPTION OF THE DRAWINGS

FIG. 3(a) to 3(d) are examples of different shapes for the knee joint bearing member.

Also in FIG. 3(c) a perspective view and FIG. 3(d) a front view, are examples of polygonal eccentric shapes of the knee joint bearing member.

FIGS. 4(a) and 4(b) show the relation of the knee plate and the knee joint bearing member when standing. FIG. 4(a) is an overall view and FIG. 4(b) is an enlarged view within the circle in FIG. 4(a).

FIG. 5 shows the relation of the knee plate and the knee joint bearing member when the knee is bent. FIG. 5(a) is an overall view and FIG. 5(b) is an enlarged view within the circle in FIG. 5(a).

FIG. 6 is a view of the knee joint bearing member of the second embodiment. FIG. 6(a) is a front view and FIG. 6(b) is a side view.

FIGS. 10(a) and 10(b) are two views showing the relation of the rotating stopper of the knee joint bearing member to the rotating stopper of the lower leg frame in an artificial leg of the conventional art when standing. In FIG. 10(a) is an overall view and FIG. 10(b) is an enlarged view within the circle in FIG. 10(a).

FIGS. 11(a) and 11(b) are two views showing the relation of the rotating stopper of the knee joint bearing member to the rotating stopper of the lower leg frame in an artificial leg of the conventional art when kneeling. In FIG. 11(a) is an overall view and FIG. 11(b) is an enlarged view within the circle in FIG. 11(a).

FIGS. 12(a) and 12(b) are two views showing the embedded status of the knee joint bearing member and the force applied to the lower leg frame. In FIG. 12(a) is the view during standing, and FIG. 12(b) is the view during kneeling.

DESCRIPTION OF THE PREFERRED EMBODIMENTS

The above described a specific example of the invention however this is not intended to limit the extent of the invention but rather to make the invention easier to understand. This invention can be freely modified or improved without deviating from the technological scope or intent of the invention.

First Embodiment

Figure 1:
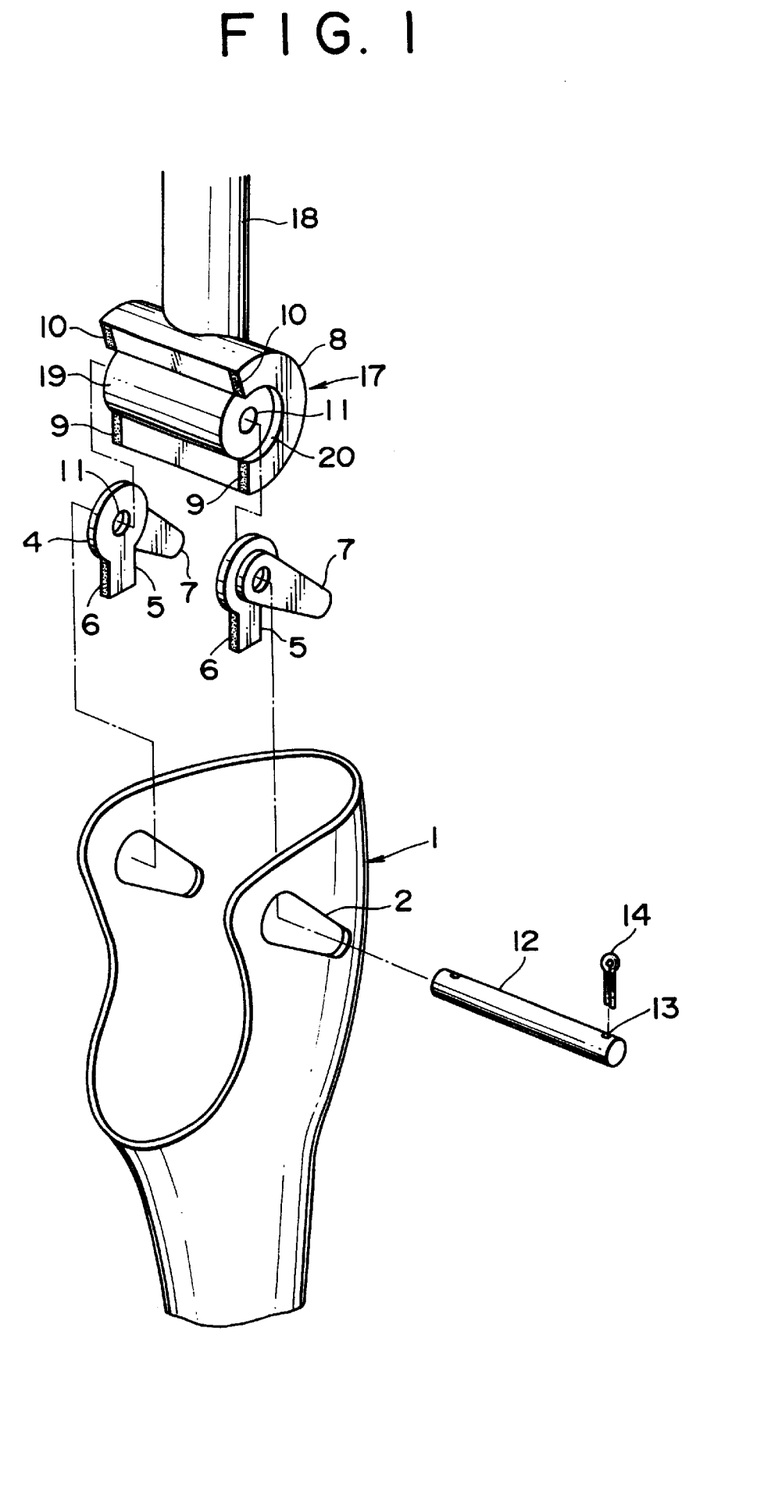
FIG. 1 is a drawing showing an artificial leg relating to this invention.

The details of the knee joint portion of the artificial leg relating to this invention are shown in FIG. 1. The lower leg frame 1 shown in FIG. 1 houses the drive mechanism for allowing the upper leg and the lower leg to perform a consecutive walking operation and further frees the rear section for consecutive contact of the socket 21 mounted in the upper leg and drive mechanism, in a knee joint portion of lower leg frame 1 whose cross section is largely formed in a U shape. This knee socket section at the upper part of the lower leg frame 1 is mounted with an opening 2 for insertion of the knee joint bearing member 4 described later. This opening 2, in order to embedably install the eccentric, egg-shaped knee joint bearing member 4 having two circles large and small connected by a common contact line; is made to the identical contour and dimensions of the eccentric knee joint bearing member 4 and further, during standing is inclined approximately 70° forwards relative to the perpendicular axial line 3 of the lower leg frame 1.

Figure 2A:
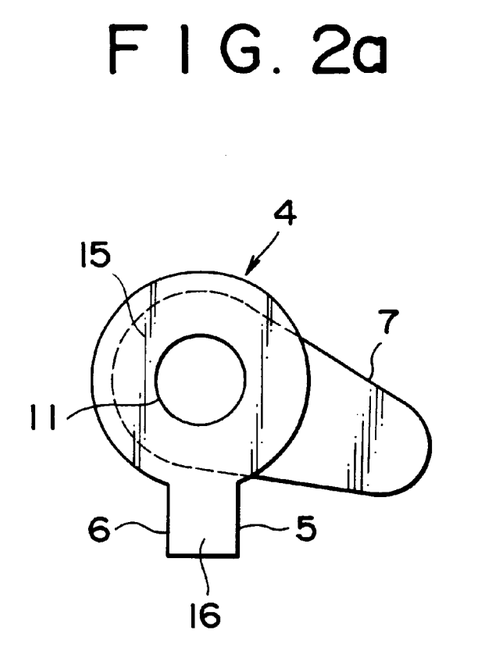
FIG. 2(a) is a front view and FIG. 2(b) is a side view showing the knee joint bearing member.
Figure 2B:
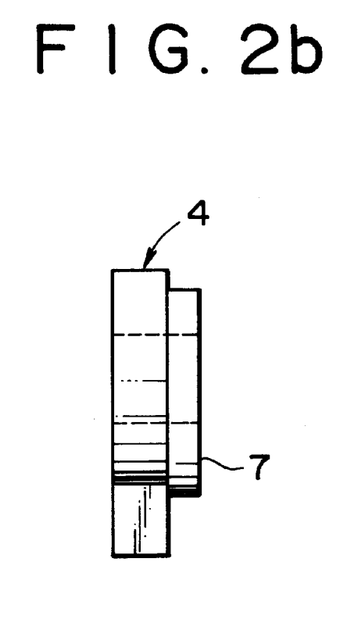

FIG. 2 shows details of the knee joint bearing member 4 integrably formed of an egg-shaped, eccentric protrusion 7 having a large circle and a small circle at a slightly separated position with center bound by a common contact line, and of a circular plate 15 in the eccentric protrusion 7, and from circular plate 15, a fixed side stopper 16 installed in a vertical downward position having parallel fixed side stopper surfaces 5 and 6 respectively for standing and kneeling, and further a through hole 11 drilled in axis 12 inside the large circle. A flange effect is achieved on a portion of the outer circumference of the circular plate 15 protruding from the eccentric protrusion 7. The knee joint bearing member 4 and the fixed side stopper 16 are mutually positioned during standing, to incline forwards approximately 70° relative to the perpendicular axial line 3 of the lower leg frame 1. Since the fixed stopper 16 in the knee joint bearing 4 must support the entire load during standing and kneeling it may be made of metals such as aluminum (including alloys) or titanium (including alloys). The said knee joint bearing 4 is embedably inserted in the opening 2 of the lower leg frame 1 so that the fixed side stopper 16 protrudes out from the side wall of the lower leg frame 1.

Figure 3A:
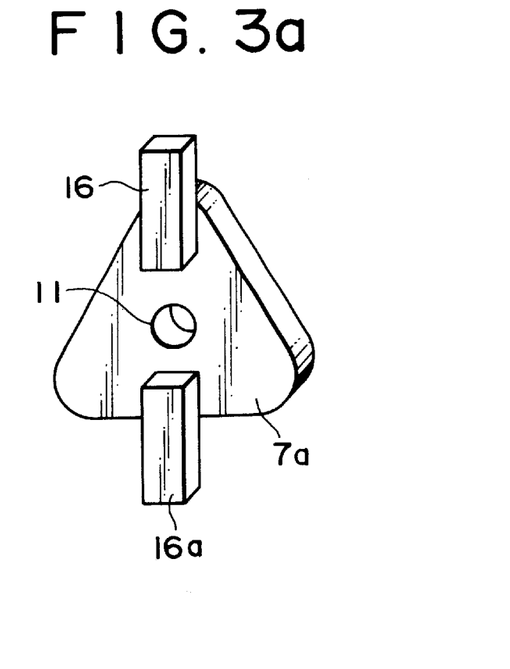
FIGS. 3(a) and 3(b) are perspective views of examples of polygonal shapes of the knee joint bearing member.
Figure 3B:
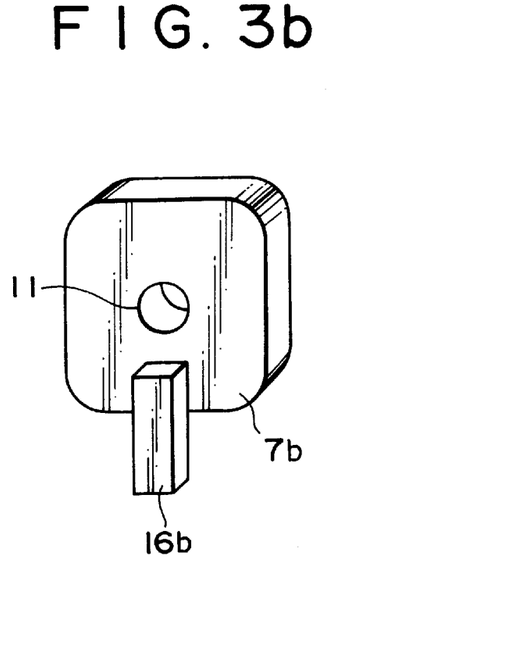
Figure 3C:
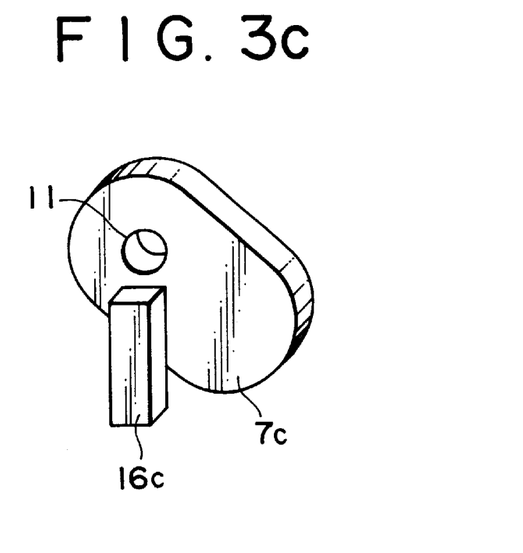
Figure 3D:
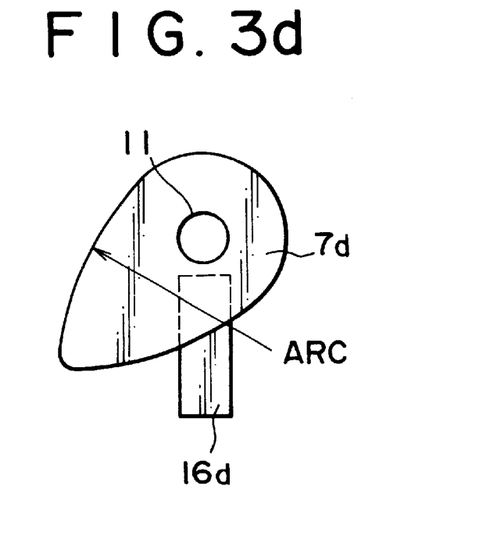

FIG. 3(a) to FIG. 3(e) show examples of typical modified shapes of the knee joint bearing 4. In FIG. 3(a), each corner of the triangle shape 7a is shaped as an arc so that fixed stoppers 16a are integrably formed respectively for standing and kneeling. In FIG. 3(b), each corner of the rectangle 7b is shaped as an arc, and a fixed stopper 16b is formed integrably. Further FIG. 3(c) and FIG. 3(d) show examples of eccentric shapes 7c and 7d for knee joint bearing member 4, with FIG. 3(c) being an oval and FIG. 3(d) being an egg shape, in either case, stoppers 16c and 16d are integrably formed respectively for standing and kneeling.

In FIG. 1, a rotating section 17 of the socket (not shown) for mounting the upper leg, is linked with the knee joint bearing member 4 embedded in the lower leg frame 1. In the embodiment in the drawing, bearing 19 is connected by way of link member 18 at the bottom of the socket. The bearing 19 is integrably assembled in the half-moon shaped knee plate 8 so that the knee plate 8 protrudes out from the bearing 19. A protrusion 20 of this knee plate 8 engages with the previously mentioned outer circumferential surface of circular plate 15 in the knee joint bearing member 4, and functions as a bearing to provide smooth rotation for the lower leg frame 1. The cutaway surfaces 9 and 10 of the knee plate 8 form a rotating stopper which maintains the stance during standing or sitting by contacting the fixed side stopper surfaces 5 and 6 installed in the knee joint bearing member 4. The axis 12 is fittably inserted from the outer side of the lower leg frame 1 and the cotter pins 14 insert in the holes 13 provided at both ends of the axis 12. A cover can be installed for protection when there is the possibility of damage to the user's clothes due to the outward protrusion of the axis 12.

Figure 4A:
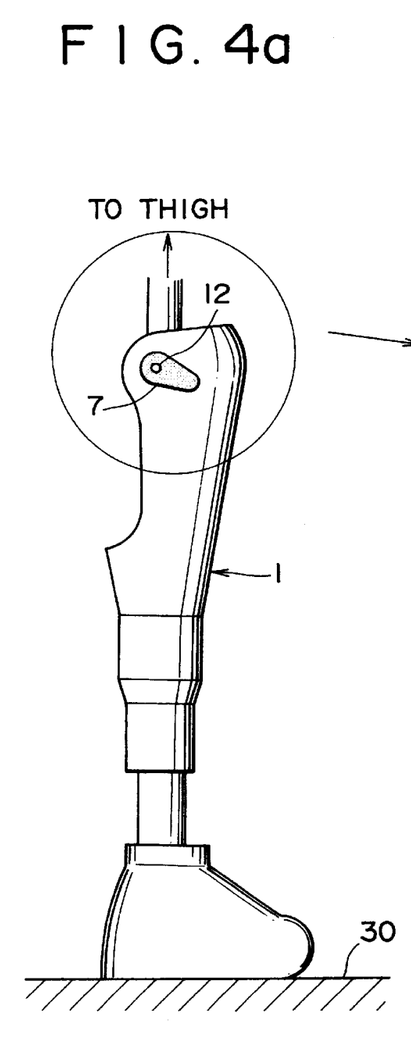
Figure 4B:
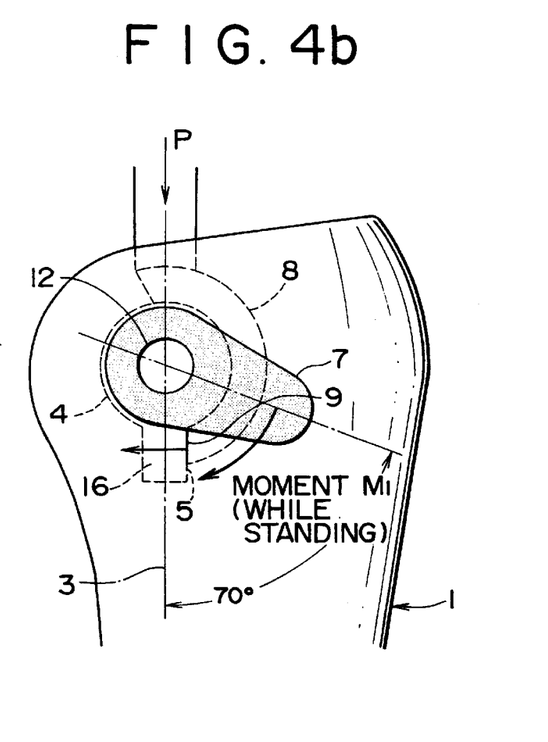
Figure 5A:
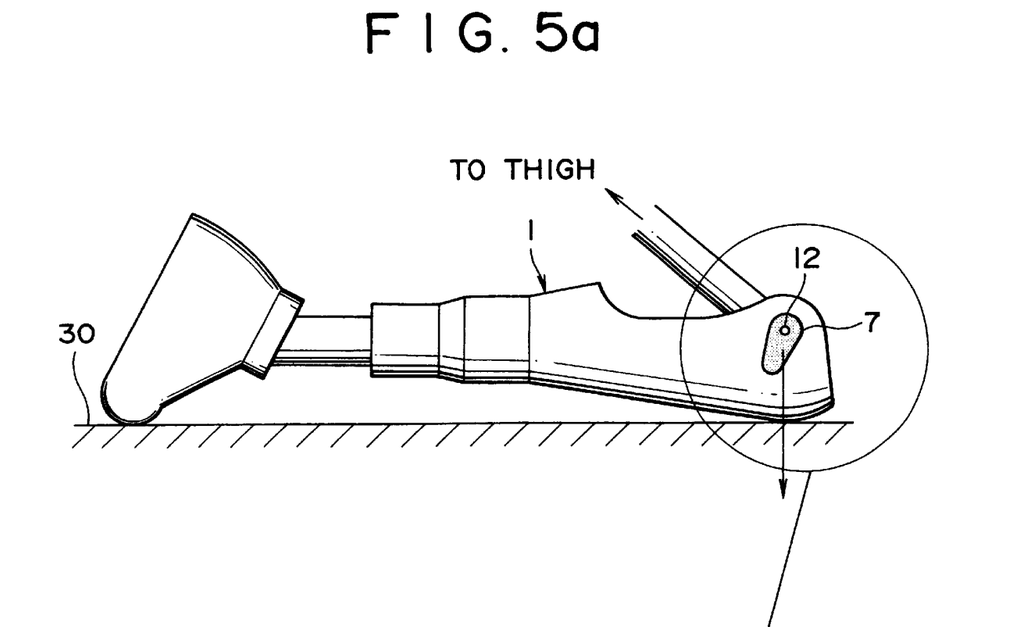
Figure 5B:
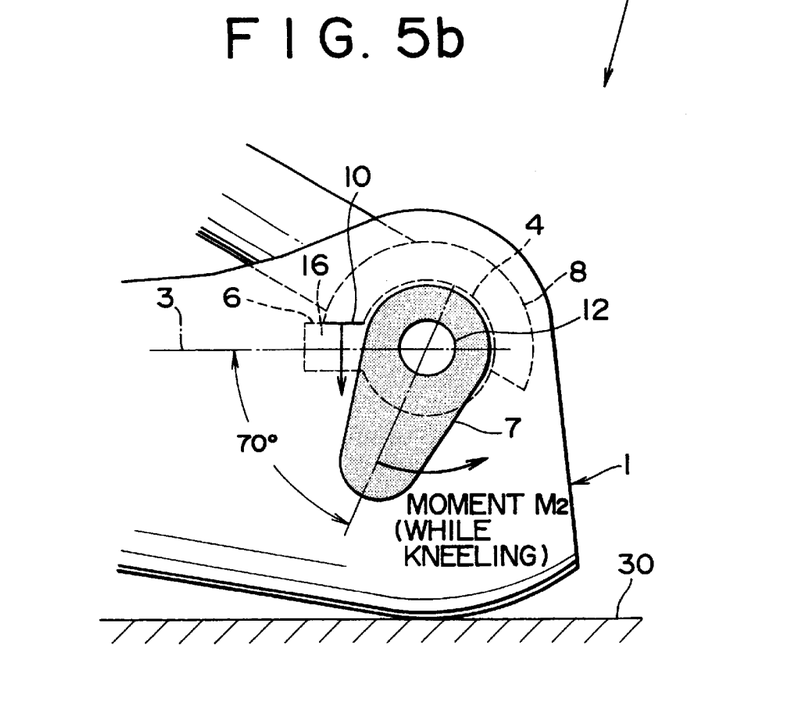

In FIGS. 4 and 5 which show the action of the artificial leg relating to this invention, during the standing position in FIG. 4, the rotating stopper surface 9 for standing, of the knee plate 8 for the rotating section 17 of the socket 21 makes contact with the fixed stopper surface 5 of the stopper 16 installed in the knee joint bearing member 4 of the lower leg frame 1 and maintains the standing position of the artificial leg.

At this time, the load acting on the lower leg frame 1 from the compressive force P due to the weight of the user, and the rotating moment M1 generated by contact of the rotating stopper surface 9 of knee plate 8 (for use during standing) with the stopper surface 5 of the fixed stopper 16 installed in the knee joint bearing member 4, are conveyed by means of the knee joint bearing member 4. The compounded load of the compressive force P and the rotating moment M1, are conveyed by the contact surfaces of the contour of eccentric protrusion 7 of the knee joint bearing member 4, and the lower leg frame 1. This arrangement in contrast to the conventional art, converts the load on the stopper mounting section from a concentrated load to a dispersed load and alleviates the load applied to points within the surface area of the lower leg frame.

FIG. 5 shows the status of the artificial leg when kneeling, in which, the rotating stopper surface 10 for kneeling, of the knee plate 8 for the rotating section 17 of the socket 21 makes contact with the fixed stopper surface 6 of the stopper 16 installed in the knee joint bearing member 4 of the lower leg frame 1 to stop excessive rotation and maintains the kneeling position of the artificial leg.

At this time, the load acting on the lower leg frame 1 from the weight of the user is a rotating moment M2, generated by contact of the rotating stopper surface 10 of the knee plate 8 (for use during kneeling) with the stopper surface 6 of the fixed stopper 16 installed in the knee joint bearing member 4. The entire moment M2 is conveyed by means of the knee joint bearing member 4. The rotating moment M2, is conveyed by the contact surfaces of the knee joint bearing member 4 contour, and the lower leg frame 1. This arrangement in contrast to the conventional art, converts the load in the vicinity of the rotating axis from a concentrated load to a dispersed load and alleviates the load applied to points within the surface area of the lower leg frame.

Second Embodiment

Figure 6A:
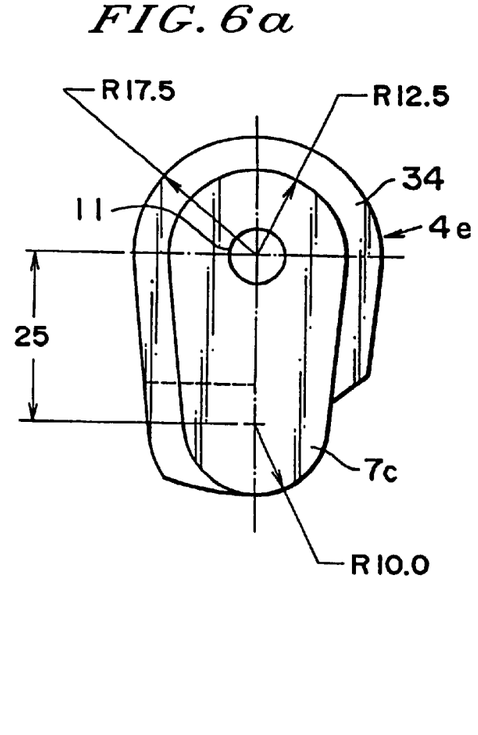
Figure 6B:
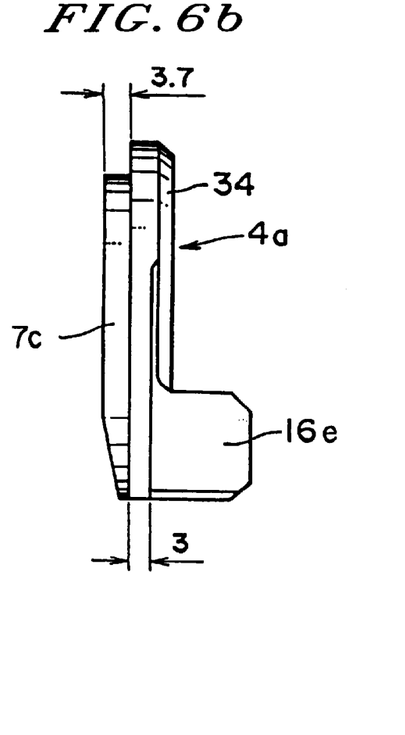

FIG. 6 shows the knee joint bearing member 4e used in the second embodiment. The knee joint bearing member 4e is integrably formed of eccentric egg-shaped protrusion 7e and flange 34 having a common contact line with the center of a small circle, and at a slightly separated position, a large circle. Fixed side stoppers 16e are provided on the said flange 34 respectively for standing and kneeling, and further a through hole 11 is drilled for the axis 12 inside the large circle. The knee joint bearing member 4e dimensions are a 12.5 mm radius for the large circle, a 10 mm radius for the small circle, a 25 mm center distance between both circles, a width of 5 mm for the flange 34 and a thickness of 3.7 mm for the eccentric protrusion 7e. The knee joint bearing member 4e is made of aluminum.

Figure 7:
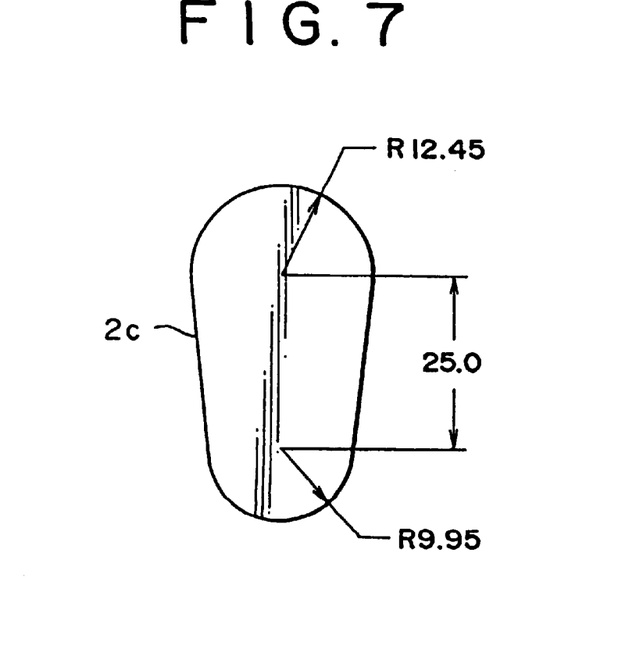
FIG. 7 is a view of the shape of the opening in the lower leg frame of the second embodiment.

The knee joint bearing member 4e is embedably inserted in the lower leg frame 1 having a thickness of 3.0 mm and as shown in FIG. 7, the dimensions for the opening 2e of the lower leg frame 1 are a 12.45 mm radius for the large circle, a 9.95 mm radius for the small circle, and a 25 mm center distance between both circles. Therefore prior to cooling and fitting, the dimension tolerance between the eccentric protrusion 7 and the opening 2e is 0.1 mm.

The knee joint bearing member 4e, being made of aluminum can be cooled and fit into the lower leg frame 1. Since the aluminum has an expansion rate of $23.7 \times 10-6/C.°$, the eccentric protrusion 7e of the knee joint bearing member 4e can be cooled and fit into place in the opening 2e of the lower leg frame 1. This cooling and fitting process allows the eccentric protrusion 7e to expand inside the opening 2e so that even if a rotating moment M1 or M2 is applied, no gap S occurs between the eccentric protrusion 2e and the opening 2e.

The user of the artificial leg will thus experience no feeling of a poor fit, and there will be no damage to the lower leg frame 1 from the generation of a gap S.

Since a flange is provided in the knee joint bearing member 4e and the thickness of the eccentric protrusion 7e is made 0.7 mm less than the lower leg frame 1, rotation of the knee joint bearing member 4e can be avoided even if lateral moment is applied to the knee joint bearing member 4e. Further, even if some rotation of knee joint bearing member 4e does occur, and there will be no increase in the contact strain, because the contact surface with the lower leg frame 1 has not decreased. The installation position of the fixed side stopper in the knee joint bearing member 4e of the first embodiment differs from the installation position of the second embodiment, however in the case of the second embodiment, this allows adjustment of the positions of the rotating stopper surface 9 of the knee plate (for standing), and the rotating stopper surface 10 (for kneeling).

Figure 8:
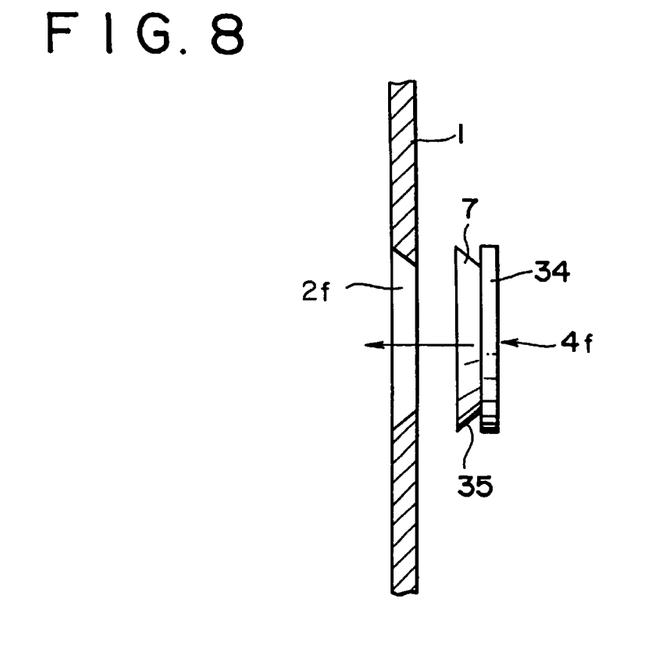
FIG. 8 is a view showing a cross section of the eccentric protrusion of the knee joint bearing member of the modified embodiment, and also a cross section of the opening in the lower leg frame.

As shown in FIG. 8, a taper 35 has been added to the outer circumferential surface of the eccentric protrusion 7f of the knee joint bearing member 4f. Note that by making the cross sectional shape of the opening 2f of the lower leg frame 1 resemble that of the cross sectional shape of the eccentric protrusion 7f, and then performing the cooling and fitting process in the direction of the arrow, the knee joint bearing member 4f can be embedably installed in the lower leg frame 1 with suitable sealing. Therefore, even if a lateral moment is applied to the knee joint bearing member 4f, a remarkable increase in strength of the lower leg frame 1 to resist destructive forces can be achieved.

What is claimed is:

1. An artificial leg, comprising:

a thigh section;

a hollow lower leg portion; and a knee joint member pivotally connecting said thigh section to said lower leg portion for rotation about an axis, wherein said knee joint member comprises:
   a) a bearing part embedded in said lower leg portion,
   b) a joint part connected to said thigh section, and
   c) an axle part cooperating with said bearing part and said joint part for permitting said lower leg portion to rotate about said axis, said joint part having a first stopper portion and a second stopper portion, wherein said bearing part has a third stopper portion positioned to engage one of said first and second stopper portions when the knee joint member is rotated to a standing position and positioned to engage the other of said first and second stopper portions when the knee joint member is rotated to a kneeling position.

2. An artificial leg according to claim 1, wherein said bearing part comprises a flange and a knee joint bearing member 0.6 to 1.0 mm thicker than the lower leg portion and embedded in the lower leg portion by differential cooling contraction.

3. The artificial leg of claim 1 wherein said bearing part has a non-circular outer periphery.

4. The artificial leg of claim 1 wherein said bearing part has a polygonal outer periphery.

5. The artificial leg of claim 4 wherein corners of the polygonal outer periphery are rounded.

6. The artificial leg of claim 1 wherein said bearing part has an elongated outer periphery in the shape of one of an oval, an ellipse and an egg shape.

7. The artificial leg of claim 6 wherein a direction of elongation of the elongated outer periphery of said bearing part is oriented about 45° to about 75° forward and upward with respect to the longitudinal axis of the lower leg portion.

* * * * *